(12) United States Patent
Kim et al.

(10) Patent No.: US 9,945,859 B2
(45) Date of Patent: Apr. 17, 2018

(54) ANTI-KRS MONOCLONAL ANTIBODY AND USE THEREOF

(71) Applicant: Medicinal Bioconvergence Research Center, Gyeonggi-do (KR)

(72) Inventors: Sunghoon Kim, Seoul (KR); Yon-Sik Choi, Seoul (KR); Hyunbo Shim, Seoul (KR); Nam Ju Lee, Gyeonggi-do (KR); Min Hwa Park, Seoul (KR)

(73) Assignee: MEDICINAL BIOCONVERGENCE RESEARCH CENTER, Geyonggi-Do (KR)

( * ) Notice: Subject to any disclaimer, the term of this patent is extended or adjusted under 35 U.S.C. 154(b) by 0 days.

(21) Appl. No.: 15/198,337

(22) Filed: Jun. 30, 2016

(65) Prior Publication Data

US 2016/0377619 A1 Dec. 29, 2016

Related U.S. Application Data

(63) Continuation of application No. PCT/KR2014/012980, filed on Dec. 29, 2014.

(30) Foreign Application Priority Data

Dec. 30, 2013 (KR) ........................ 10-2013-0166791

(51) Int. Cl.
*C07K 16/40* (2006.01)
*G01N 33/573* (2006.01)
*G01N 33/574* (2006.01)
*G01N 33/564* (2006.01)

(52) U.S. Cl.
CPC .......... *G01N 33/573* (2013.01); *C07K 16/40* (2013.01); *G01N 33/564* (2013.01); *G01N 33/57488* (2013.01); *C07K 2317/33* (2013.01); *C07K 2317/56* (2013.01); *C07K 2317/565* (2013.01); *C07K 2317/622* (2013.01); *C07K 2317/92* (2013.01)

(58) Field of Classification Search
None
See application file for complete search history.

(56) References Cited

U.S. PATENT DOCUMENTS

| 4,737,456 | A | 4/1988 | Weng et al. |
| 4,816,567 | A | 3/1989 | Cabilly et al. |
| 4,946,778 | A | 8/1990 | Ladner et al. |
| 5,258,498 | A | 11/1993 | Huston et al. |
| 5,260,203 | A | 11/1993 | Ladner et al. |
| 5,939,598 | A | 8/1999 | Kucherlapati et al. |
| 2013/0243745 | A1 | 9/2013 | Greene et al. |

FOREIGN PATENT DOCUMENTS

| EP | 183070 A2 | 6/1986 |
| EP | 244234 A2 | 11/1987 |
| EP | 402226 A1 | 12/1990 |
| EP | 0404097 A2 | 12/1990 |
| KR | 1020080099783 | 1/2011 |
| WO | 1988001649 A1 | 3/1988 |
| WO | 1992022324 A1 | 12/1992 |
| WO | 1993011161 A1 | 6/1993 |

OTHER PUBLICATIONS

Gelpi, Carmen et al., Coexistence of Two Antisynthetases in a Patient with the Antisynthetase Syndrome, Arthritis & Rheumatism, Apr. 4, 1996, p. 692-697, vol. 39, No. 4, American College of Rheumatology, Atlanta, GA.

Chothia, Cyrus et al., Canonical Structures for the Hypervariable Regions of Immunoglobulins, Journal of Molecular Biology, Aug. 20, 1987, p, 901-917, vol. 196, Issue 4, Academic Press Limited, Cambridge, MA.

Clackson, Tim et al., Making Antibody Fragments Using Phage Display Libraries, Letters to Nature, Aug. 15, 1991, p. 624-628, vol. 352, Nature, United Kingdom.

Holliger, Philipp et al., "Diabodies":Small Bivalent and Bispecific Antibody Fragments, Proceedings of the National Academy of Sciences of the United States of America, Jul. 1993, p. 6444-6448, vol. 90 No. 14, United States National Academy of Sciences, Washington D.C.

Kohler, G. et al., Continuous Cultures of Fused Cells Secreting Antibody of Predefined Specificity, Nature, Aug. 7, 1975, p. 495-497, vol. 256, Nature Publishing Group, United Kingdom.

Kunst, Catherine et al., Mutations in SOD1 Associated with Amyotrophic Lateral Sclerosis Cause Novel Protein Interactions, Nature Genetics, Jan. 15, 1997, p. 91-94, vol. 15, Nature Publishing Group, United Kingdom.

Marks, James D. et al., By-passing Immunization Human Antibodies from V-gene Libraries Displayed on Phage, Journal of Molecular Biology, 1991, p. 581-597, vol. 222, Academic Press Limited, Cambridge, MA.

Morrison, Sherie L. et al., Chimeric Human Antibody Molecules: Mouse Antigen-binding Domains with Human Constant Region Domains, Proceedings of the National Academy of Sciences of the United States of America, Nov. 1984, p. 6851-6855, vol. 81, United States National Academy of Sciences, Washington D.C.

(Continued)

Primary Examiner — Daniel C Gamett
(74) Attorney, Agent, or Firm — Levenfeld Pearlstein, LLC

(57) ABSTRACT

The present invention relates to an anti-lysyl-tRNA synthetase (KRS) antibody selectively binding to KRS, and a use thereof and, more specifically, to an antibody binding to human KRS or a fragment thereof, a method for producing the same, and a composition containing the same for diagnosing cancer, autoimmune diseases or inflammatory diseases. The antibody or fragment thereof of the present invention specifically binds to human KRS, and enables KRS detection and inhibition due to the absence of cross-linkage reactivity with the other proteins including the same ARS family, and thus the antibody or fragment thereof can be used to detect KRS and diagnose KRS-related diseases, i.e., cancer, autoimmune diseases or inflammatory diseases.

12 Claims, 6 Drawing Sheets

(56) References Cited

OTHER PUBLICATIONS

Presta, Leonard G., Selection, Design, and Engineering of Therapeutic Antibodies, Journal of Allergy and Clinical Immunology, Oct. 2005, p. 731-736, vol. 116, No. 4, Mosby Imprint, Maryland Heights, MO.

Park, Sang Gyu et al., Human lysyl-tRNA Synthetase is Secreted to Trigger Proinflammatory Response, Proceedings of the National Academy of Sciences of the United States of America, May 3, 2005, p. 6356-6361, vol. 102, No. 18, United States National Academy of Sciences, Washington D.C.

Zapata, Gerardo et al., Engineering Linear F(ab')2 Fragments for Efficient Production in *Escherichia coli* and Enhanced Antiproliferative Activity, Protein Engineering, 1995, p. 1057-1062, vol. 8, No. 10, Oxford University Press, United Kingdom.

Yoshifuji, Hajime et al., Anti-aminoacyl-tRNA Synthetase Antibodies in Clinical Course Prediction of Interstitial Lung Disease Complicated with Idiopathic Inflammatory Myopathies, Autoimmunity, May 2006, p. 233-241, vol. 39, No. 3, Informa Healthcare, United Kingdom.

Matsushita, Takashi et al., Clinical Evaluation of Anti-aminoacyl tRNA Synthetase Antibodies in Japanese Patients with Dermatomyositis, The Journal of Rheumatology, 2007, p. 1012-1018, vol. 34, No. 5, The Journal of Rheumatology Publishing Company Limited, Canada.

FIG. 3

SEQUENCE LISTING

<160> NUMBER OF SEQ ID NOS: 14

<210> SEQ ID NO 1
<211> LENGTH: 13
<212> TYPE: PRT
<213> ORGANISM: Artificial Sequence
<220> FEATURE:

<223> OTHER INFORMATION: VL-CDR1 of Biocon K1

<400> SEQUENCE: 1

Ser Gly Ser Ser Ser Asn Ile Gly Asn Asn Thr Val Ser
1               5                   10

<210> SEQ ID NO 2
<211> LENGTH: 7
<212> TYPE: PRT
<213> ORGANISM: Artificial Sequence
<220> FEATURE:
<223> OTHER INFORMATION: VL-CDR2 of Biocon G1

<400> SEQUENCE: 2

Ala Asn Ser Lys Arg Pro Ser
1               5

<210> SEQ ID NO 3
<211> LENGTH: 11
<212> TYPE: PRT
<213> ORGANISM: Artificial Sequence
<220> FEATURE:
<223> OTHER INFORMATION: VL-CDR3 of Biocon K1

<400> SEQUENCE: 3

Gly Ala Trp Asp Ser Ser Leu Ser Gly Tyr Val
1               5                   10

<210> SEQ ID NO 4
<211> LENGTH: 5
<212> TYPE: PRT
<213> ORGANISM: Artificial Sequence
<220> FEATURE:
<223> OTHER INFORMATION: VH-CDR1 of Biocon K1

<400> SEQUENCE: 4

Asn Tyr Ala Met Ser
1               5

<210> SEQ ID NO 5
<211> LENGTH: 17
<212> TYPE: PRT
<213> ORGANISM: Artificial Sequence
<220> FEATURE:
<223> OTHER INFORMATION: VH-CDR2 of Biocon K1

<400> SEQUENCE: 5

Gly Ile Ser Pro Ser Ser Gly Asp Thr Tyr Tyr Ala Asp Ser Val Lys
1               5                   10                  15

Gly

<210> SEQ ID NO 6
<211> LENGTH: 12
<212> TYPE: PRT
<213> ORGANISM: Artificial Sequence
<220> FEATURE:
<223> OTHER INFORMATION: VH-CDR3 of Biocon K1

<400> SEQUENCE: 6

Gly Val Trp Trp Tyr His Pro Leu Leu Phe Asp Tyr
1               5                   10

<210> SEQ ID NO 7
<211> LENGTH: 39
<212> TYPE: DNA
<213> ORGANISM: Artificial Sequence

```
<220> FEATURE:
<223> OTHER INFORMATION: VL-CDR1 of Biocon K1

<400> SEQUENCE: 7
agtggctctt catctaatat tggcaataat actgtctcc                                      39

<210> SEQ ID NO 8
<211> LENGTH: 21
<212> TYPE: DNA
<213> ORGANISM: Artificial Sequence
<220> FEATURE:
<223> OTHER INFORMATION: VL-CDR2 of Biocon K1

<400> SEQUENCE: 8
gctaatagta agcggccaag c                                                         21

<210> SEQ ID NO 9
<211> LENGTH: 33
<212> TYPE: DNA
<213> ORGANISM: Artificial Sequence
<220> FEATURE:
<223> OTHER INFORMATION: VL-CDR3 of Biocon K1

<400> SEQUENCE: 9
ggtgcttggg attctagcct gagtggttat gtc                                            33

<210> SEQ ID NO 10
<211> LENGTH: 15
<212> TYPE: DNA
<213> ORGANISM: Artificial Sequence
<220> FEATURE:
<223> OTHER INFORMATION: VH-CDR1 of Biocon K1

<400> SEQUENCE: 10
aattatgcta tgagc                                                                15

<210> SEQ ID NO 11
<211> LENGTH: 51
<212> TYPE: DNA
<213> ORGANISM: Artificial Sequence
<220> FEATURE:
<223> OTHER INFORMATION: VH-CDR2 of Biocon K1

<400> SEQUENCE: 11
gggatctctc ctagtagtgg tgatacatat tacgctgatt ctgtaaaagg t                        51

<210> SEQ ID NO 12
<211> LENGTH: 36
<212> TYPE: DNA
<213> ORGANISM: Artificial Sequence
<220> FEATURE:
<223> OTHER INFORMATION: VH-CDR3 of Biocon K1

<400> SEQUENCE: 12
ggtgtttggt ggtatcatcc tttgctgttc gactac                                         36

<210> SEQ ID NO 13
<211> LENGTH: 246
<212> TYPE: PRT
<213> ORGANISM: Artificial Sequence
<220> FEATURE:
<223> OTHER INFORMATION: scFv of Biocon K1
```

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Ser Pro Ser Ser Gly Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Trp Trp Tyr His Pro Leu Leu Phe Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gln Ser Val Leu Thr Gln Pro Pro
    130                 135                 140

Ser Ala Ser Gly Thr Pro Gly Gln Arg Val Thr Ile Ser Cys Ser Gly
145                 150                 155                 160

Ser Ser Ser Asn Ile Gly Asn Asn Thr Val Ser Trp Tyr Gln Gln Leu
                165                 170                 175

Pro Gly Thr Ala Pro Lys Leu Leu Ile Tyr Ala Asn Ser Lys Arg Pro
            180                 185                 190

Ser Gly Val Pro Asp Arg Phe Ser Gly Ser Lys Ser Gly Thr Ser Ala
        195                 200                 205

Ser Leu Ala Ile Ser Gly Leu Arg Ser Glu Asp Glu Ala Asp Tyr Tyr
    210                 215                 220

Cys Gly Ala Trp Asp Ser Ser Leu Ser Gly Tyr Val Phe Gly Gly Gly
225                 230                 235                 240

Thr Lys Leu Thr Val Leu
            245

<210> SEQ ID NO 14
<211> LENGTH: 738
<212> TYPE: DNA
<213> ORGANISM: Artificial Sequence
<220> FEATURE:
<223> OTHER INFORMATION: scFv of Biocon K1

<400> SEQUENCE: 14
gaggtgcagc tgttggagtc cggggggaggc ttggtacagc ctgggggggtc cctgagactc     60 tcctgtgcag cctctggatt caccttttagc aattatgcta tgagctgggt ccgccaggct    120
ccagggaagg gctggagtg gtctcaggg atctctccta gtagtggtga tacatattac    180
gctgattctg taaaaggtcg gttcaccatc tccagggaca attccaagaa cacgctgtat    240
ctgcaaatga acagcctgag agccgaggac acggccgtgt attactgtgc gaaaggtgtt    300
tggtggtatc atcctttgct gttcgactac tggggccagg gtacactggt caccgtgagc    360
tcaggtggag gcggttcagg cggaggtgga tccggcggtg gcggatcgca gtctgtgctg    420
actcagccgc cctcagcgtc tgggaccccc gggcagaggg tcaccatctc ttgtagtggc    480
tcttcatcta atattggcaa taatactgtc tcctggtacc agcagctccc aggaacggcc    540

| | | | | |
|---|---|---|---|---|
| cccaaactcc | tcatctatgc | taatagtaag cggccaagcg | gggtccctga ccgattctct | 600 |
| ggctccaagt | ctggcacctc | agcctccctg gccatcagtg | ggctccggtc cgaggatgag | 660 |
| gctgattatt | actgtggtgc | ttgggattct agcctgagtg | gttatgtctt cggcggaggc | 720 |
| accaagctga | cggtccta | | | 738 |

ANTI-KRS MONOCLONAL ANTIBODY AND USE THEREOF

This application is a continuation of PCT Application No. PCT/KR2014/012980, filed Dec. 29, 2014, which claims the benefit of and priority to Korean Patent Application No. 10-2013-0166791, filed Dec. 30, 2013, the contents of which are incorporated fully by reference herein.

TECHNICAL FIELD

The present invention relates to an anti-lysyl-tRNA synthetase (KRS) antibody selectively binding to KRS and a use thereof and, more particularly, to an antibody or fragment thereof that binds to human KRS, a method for preparing the same, and a composition containing the same for diagnosing cancer, an autoimmune disease, or an inflammatory disease.

BACKGROUND ART

Aminoacyl-tRNA synthetases (ARSs) are enzymes that attach specific amino acids onto their corresponding tRNAs, respectively. In higher organisms, the aminoacyl-tRNA synthetases include 23 types of enzymes, including three types involved in the formation of multisynthetase complex, such as AIMP1(p43), (AIMP2)p38, and (AIMP3)p18, in addition to 20 types of enzymes according to the kind of amino acid, while several enzymes, excluding the enzymes involved in the formation of multisynthetase complex, may be also present in a free form. Recently, aminoacyl-tRNA synthetases have been reported to possess, besides their basic functions, various other activation functions in particular environments, one of which is lysyl-tRNA synthetase (KRS). It has been revealed that KRS induces an immune response through macrophage activation. It has been reported that KRS secreted from cells by TNF-α increases the activity of macrophages by TNF-α or cellular migration through signaling by p38 mitogen activated kinase or the like. Also, KRS has been recently revealed to be involved in various diseases. It has been reported that autoantibodies to KRS are present in inflammatory muscle disease patients, while KRS is involved in Lou Gehrig's disease by binding to SOD1 in patients with SOD1 gene mutation causing Lou Gehrig's disease. It has been recently reported that phosphorylated KRS in cancer cells contributes to the stabilization of Laminin receptors to promote the metastasis of cancer cells. Such results show that KRS may be present in the serum of autoimmune disease patients and cancer patients and may be used as a key diagnostic biomarker.

However, in spite of the importance of ARSs including KRS as biomarkers, ARSs are similar in their protein structures, and thus the antibodies obtained from animals through the immune response show a cross-linkage reaction binding with even other ARSs, and in many cases, high-sensitivity antibodies may not be generated. The antibodies of the present invention are expected to be highly applicable in the search, diagnosis, and industry since they have excellent sensitivity and no cross reaction between ARSs.

DETAILED DESCRIPTION OF THE INVENTION

Technical Problem

While being in search for antibodies specifically binding to KRS, the present inventors have discovered fragments specifically binding to KRS, from libraries constructed by a phage display method, and established their sequences and binding specificity, and thus have completed the present invention.

Therefore, an aspect of the present invention is to provide an antibody or fragment thereof that binds to human KRS.

Another aspect of the present invention is to provide a polynucleotide encoding the antibody or fragment thereof.

Still another aspect of the present invention is to provide a vector containing the polynucleotide.

Another aspect of the present invention is to provide cells having the vector.

Another aspect of the present invention is to provide a method for preparing an antibody or fragment thereof that binds to human KRS.

Still another aspect of the present invention is to provide a KRS-specific detection method comprising: bringing an antibody or a fragment thereof into contact with a sample; and detecting the antibody or fragment thereof.

Another aspect of the present invention is to provide a composition for diagnosing cancer comprising the antibody or fragment thereof as an active ingredient.

Another aspect of the present invention is to provide a composition for diagnosing an autoimmune disease comprising the antibody or fragment thereof as an active ingredient.

Still another aspect of the present invention is to provide a composition for diagnosing an inflammatory disease comprising the antibody or fragment thereof as an active ingredient.

Technical Solution

In accordance with an aspect of the present invention, there is provided an antibody or fragment thereof that binds to human KRS, the antibody comprising:

an antibody light chain variable region (VL) comprising complementarity-determining region (CDR) L1 including the amino acid sequence represented by SEQ ID NO: 1, complementarity-determining region (CDR) L2 including the amino acid sequence represented by SEQ ID NO: 2, and complementarity-determining region (CDR) L3 including the amino acid sequence represented by SEQ ID NO: 3; and an antibody heavy chain variable region (VH) comprising complementarity-determining region (CDR) H1 including the amino acid sequence represented by SEQ ID NO: 4, complementarity-determining region (CDR) H2 including the amino acid sequence represented by SEQ ID NO: 5, and complementarity-determining region (CDR) H3 including the amino acid sequence represented by SEQ ID NO: 6.

In accordance with another aspect of the present invention, there is provided a polynucleotide encoding the antibody or fragment thereof.

In accordance with another aspect of the present invention, there is provided a vector comprising the polynucleotide.

In accordance with another aspect of the present invention, there is provided a cell comprising the vector.

In accordance with another aspect of the present invention, there is provided a method for preparing an antibody or fragment thereof that binds to human KRS, the method comprising:

culturing the cell under conditions where a polynucleotide is expressed, thereby preparing a polypeptide comprising light-chain and heavy-chain variable regions; and collecting the polypeptide from the cell or a culture medium in which the cell is cultured.

In accordance with still another aspect of the present invention, there is provided a KRS-specific detection method comprising:

bringing the antibody or fragment thereof into contact with a sample; and detecting the antibody or fragment thereof.

In accordance with still further another aspect of the present invention, there is provided a composition for diagnosing a cancer comprising the antibody or fragment thereof as an active ingredient.

In accordance with another aspect of the present invention, there is provided a use of the antibody or fragment thereof for preparing an agent for cancer diagnosis.

In accordance with still another aspect of the present invention, there is provided a method for diagnosing a cancer in a subject, the method comprising:

(a) obtaining a biological sample from a subject;

(b) determining the level of KRS protein in the biological sample using the antibody or fragment thereof; and (c) comparing the determined level of KRS protein with the level of KRS protein in a normal subject.

In accordance with another aspect of the present invention, there is provided a composition for diagnosing an autoimmune disease comprising the antibody or fragment thereof as an active ingredient.

In accordance with still another aspect of the present invention, there is provided a use of the antibody or fragment thereof for preparing an agent for autoimmune disease diagnosis.

In accordance with still further another aspect of the present invention, there is provided a method for diagnosing an autoimmune disease in a subject, the method comprising:

(a) obtaining a biological sample from a subject;

(b) determining the level of KRS protein in the biological sample using the antibody or fragment thereof; and (c) comparing the determined level of KRS protein with the level of KRS protein in a normal subject.

In accordance with another aspect of the present invention, there is provided a composition for diagnosing an inflammatory disease comprising the antibody or fragment thereof as an active ingredient.

In accordance with still another aspect of the present invention, there is provided a use of the antibody or fragment thereof for preparing an agent for inflammatory disease diagnosis.

In accordance with still further another aspect of the present invention, there is provided a method for diagnosing an inflammatory disease in a subject, the method comprising:

(a) obtaining a biological sample from a subject;

(b) determining the level of KRS protein in the biological sample using the antibody or fragment thereof; and (c) comparing the determined level of KRS protein with the level of KRS protein in a normal subject.

Hereinafter, the present invention will be described in detail.

The present invention provides an antibody or fragment thereof that binds to human KRS, the antibody comprising:

an antibody light chain variable region (VL) comprising complementarity-determining region (CDR) L1 including the amino acid sequence represented by SEQ ID NO: 1, complementarity-determining region (CDR) L2 including the amino acid sequence represented by SEQ ID NO: 2, and complementarity-determining region (CDR) L3 including the amino acid sequence represented by SEQ ID NO: 3; and an antibody heavy chain variable region (VH) comprising complementarity-determining region (CDR) H1 including the amino acid sequence represented by SEQ ID NO: 4, complementarity-determining region (CDR) H2 including the amino acid sequence represented by SEQ ID NO: 5, and complementarity-determining region (CDR) H3 including the amino acid sequence represented by SEQ ID NO: 6.

Lysyl-tRNA synthetase (KRS) is an enzyme that promotes a binding between lysine (Lys) and tRNA, and is a type of aminoacyl-tRNA-synthetase (ARS). As used herein, KRS generally includes natural type or recombinant human KRS, and non-human analogues of human KRS.

As used herein, the terms "antibody", "anti-KRS antibody", "humanized anti-KRS antibody", and "modified humanized anti-KRS antibody" are used in their broadest senses, and encompass monoclonal antibodies (including full-length monoclonal antibodies), polyclonal antibodies, multi-specific antibodies (e.g., bispecific antibodies), and antibody fragments thereof (e.g., variable regions and other regions of the antibody exhibiting target biological activities (e.g., binding with KRS)).

The antibody according to an aspect of the present invention may have particular amino acid sequences included in light chain and heavy chain CDRs, so that the antibody can selectively bind to KRS, while encompassing both a monoclonal antibody and a polyclonal antibody, and may be preferably a monoclonal antibody. In addition, the antibody according to an aspect of the present invention may include chimeric antibodies, humanized antibodies, and human antibodies, and may be preferably a human antibody.

As used herein, the monoclonal antibodies represent antibodies obtained from a population of substantially homogenous antibodies. In other words, individual antibodies constituting the population are the same, excluding mutants that may be naturally present in a small quantity. The monoclonal antibodies bind to a single antigen epitope in a significantly specific manner.

The term "monoclonal" refers to characteristics of an antibody, such as obtaining antibodies from a substantially homogenous population, and is not construed as requiring the production of an antibody by a particular method.

For example, the monoclonal antibodies as used herein may be prepared by the hybridoma method first described by Kohler et al. (1975) Nature 256:495), or may be prepared by a recombinant DNA method (see, e.g., U.S. Pat. No. 4,816,567). The monoclonal antibodies may also be isolated from phage antibody libraries using the techniques described in, for example, Clackson et. al. (1991) Nature 352:624-628; Marks et al. (1991) J Mol. Biol. 222:581-597; and Presta (2005) J. Allergy Clin. Immunol. 116:731.

Specifically, the antibody according to an aspect of the present invention includes, specifically, chimeric antibodies, and in these cases, a portion of the heavy and/or light chain is identical with or homologous to corresponding sequences in antibodies derived from a particular species or a particular antibody class, while the rest portion of the chain(s) is identical with or homologous to corresponding sequences in antibodies derived from another species or another antibody class, so long as the antibody according to an aspect of the present invention exhibits desired biological activity (e.g., selective binding with KRS) (see, U.S. Pat. No. 4,816,567 and Morrison et. al., (1984) Proc. Natl. Acad. Sci. USA 81: 6851-6855).

Humanized antibodies include both sequences of human and non-human (e.g., rat) antibodies, and generally, other regions excluding epitope-binding regions (CDRs) may be derived from the human antibody and the epitope-binding regions (CDRs) may comprise non-human derived sequences.

A complete human antibody refers to an antibody containing solely human immunoglobulin protein sequences, and may be prepared in mice, mouse cells, or hybridomas originated from mouse cells, or may be prepared by a phage display method.

Natural antibodies produced in vivo are usually heterotetrameric glycoproteins of about 150,000 Da which are composed of two identical light (L) chains and two identical heavy (H) chains. Each light chain is linked to the heavy chain by one covalent disulfide bond, while the number of disulfide linkages varies among the heavy chains of different immunoglobulin isotypes. Each heavy and light chain also have regularly spaced intra-chain disulfide bridges. Each heavy chain has, at one end, a variable domain (VH) followed by a number of constant domains. Each light chain has a variable domain at one end and a constant domain at the other end; the constant domain of the light chain is aligned with the first constant domain of the heavy chain, and the light chain variable domain is aligned with the variable domain of the heavy chain. Particular amino acid residues are believed to form an interface between the light chain variable domain and the heavy chain variable domain.

The "variable region" or "variable domain" of the antibody refers to an amino-terminal domain of its heavy or light chain. The variable region of the heavy chain is indicated as "VH", while the variable region of the light chain is indicated as "VL". These domains are generally the most variable portions of the antibody, and contain antigen-binding sites.

The term "hypervariable" refers to the fact that several sequences within the variable regions differ extensively in sequence among antibodies and contain residues that are directly involved in the binding and specificity of each particular antibody for its specific antigenic determinant.

The hypervariability, both in the light chain and the heavy chain variable regions, is concentrated in three segments known as complementarity determining regions (CDRs) or hypervariable loops (HVLs). CDRs are defined by sequence comparison in Kabat et al., 1991, In: Sequences of Proteins of Immunological Interest, 5th Ed. Public Health Service, National Institutes of Health, Bethesda, Md., whereas HVLs are structurally defined according to the three-dimensional structure of the variable domain, as described by Chothia and Lesk, 1987, J. Mol. Biol. 196: 901-917. As defined by Kabat, CDR-L1 is positioned about at residues 24-34, CDR-L2 about at residues 50-56, and CDR-L3 about at residues 89-97 in the light chain variable domain; and CDR-H1 is positioned about at residues 31-35, CDR-H2 about at residues 50-65, and CDR-H3 about at residues 95-102 in the heavy chain variable domain.

Three CDRs in each heavy chain and light chain are separated by frame regions (FRs) which contain sequences having less variable tendency. From the amino terminal to the carboxy terminal of each heavy chain and light chain variable region, FRs and CDRs are arranged in the following order: FR1, CDR1, FR2, CDR2, FR3, CDR3, and FR4. The large β-sheet configuration of the FR brings the CDRs within each of the chains into close proximity to each other as well as to the CDRs from the other chain. The generated conformation contributes to the antigen binding site (see Kabat et al., 1991, NIH Publ. No. 91-3242, Vol. I, pages 647-669), while all CDR residues are not needed to be directly involved in antigen binding.

The antibody according to an aspect of the present invention is characterized by specifically binding to KRS since the CDRs pertaining to the light chain and heavy chain variable regions comprise particular sequences, respectively. Specifically, the antibody according to an aspect of the present invention may be an antibody comprising:

an antibody light chain variable region (VL) comprising complementarity-determining region (CDR) L1 including the amino acid sequence represented by SEQ ID NO: 1, complementarity-determining region (CDR) L2 including the amino acid sequence represented by SEQ ID NO: 2, and complementarity-determining region (CDR) L3 including the amino acid sequence represented by SEQ ID NO: 3; and an antibody heavy chain variable region (VH) comprising complementarity-determining region (CDR) H1 including the amino acid sequence represented by SEQ ID NO: 4, complementarity-determining region (CDR) H2 including the amino acid sequence represented by SEQ ID NO: 5, and complementarity-determining region (CDR) H3 including the amino acid sequence represented by SEQ ID NO: 6.

Preferably, the antibody according to an aspect of the present invention may comprise particular light and heavy chain variable regions, and may contain the 137th to 246th amino acid residues of the amino acid sequence of SEQ ID NO: 13 for the light chain variable region and the $1^{st}$ to the 121st amino acid residues of the amino acid sequence of SEQ ID NO: 13 for the heavy chain variable region.

Most preferably, the antibody according to an aspect of the present invention may comprise the amino acid sequence represented by SEQ ID NO: 13.

The antibody fragment, fragment, or "fragment thereof" as used herein include fragments or derivatives of the antibody retaining at least a portion of the binding specificity of an antibody, which typically contain at least a portion of an antigen binding region or a variable region (e.g., at least one CDR) of an antibody. Examples of the antibody fragment include Fab, Fab', F(ab')$_2$, and Fv fragments; diabodies; linear antibodies; single-chain antibody molecules, e.g., sc-Fv fragments; and multi-specific antibodies formed from the antibody fragments, but are not limited thereto. Typically, the antibody fragment or derivative retains at least 10% of MRS binding activity when its activity is expressed in terms of mole. Preferably, the antibody fragment or derivative retains at least 20%, 50%, 70%, 80%, 90%, 95%, or 100% of MRS binding affinity of the antibody. In addition, the MRS antibody fragment may include conservative amino acid substitutions (also called conservative variants of the antibody) of which biological activity is not substantially changed. The "binding compound" as used herein indicates both an antibody and a fragment thereof.

The Fab fragment is composed of one single light chain, and the CH1 domain (first constant domain) and a variable region of one single heavy chain. The heavy chain of the Fab molecule cannot form a disulfide linkage with another heavy chain.

The Fc region contains two heavy-chain fragments each having CH2 and CH3 domains. Two heavy-chain fragments are maintained by two or more disulfide linkages and the hydrophobic interaction between CH3 domains.

The Fab' fragment contains one light chain, and a portion of one heavy chain that contains the VH domain and the CH1 domain and also a region between the CH1 and CH2 domains, such that an inter-chain disulfide linkage can be formed between the two heavy chains of two Fab' fragments to form an F(ab')$_2$ molecule.

The F(ab')2 fragment contains two light chains, and two heavy chains containing a portion of the constant region between the CH1 and CH2 domains, such that an inter-chain disulfide linkage is formed between the two heavy chains. The F(ab')2 fragment is thus composed of two Fab' fragments that are maintained together by a disulfide linkage between the two heavy chains.

The Fv region contains the variable regions from both the heavy and light chains, but lacks the constant regions.

The single-chain Fv or scFv fragment represents an antibody fragment that contains VH and VL domains of the antibody, and here, these domains are present in the single polypeptide chain. Generally, the Fv polypeptide further contains a polypeptide linker positioned between the VH and VL domains so as to form a desired structure for antigen binding by the scFv fragment. For the summary of scFv, see Pluckthun (1994) THE PHARMACOLOGY OF MONOCLONAL ANTIBODIES, vol. 113, Rosenburg and Moore eds. Springer-Verlag, New York, pp. 269-315. Also, see PCT publication NO. 1988/001649 and U.S. Pat. Nos. 4,946,778 and 5,260,203.

As used herein, the diabody refers to a small antibody fragment having two antigen-binding sites, and here, the fragment contains a heavy chain variable domain (VH) concatenated to a light chain variable region (VL) (VH-VL) on the same polypeptide chain. By using a linker that is too short to allow pairing between the two domains on the same chain, the linked VH-VL domains are forced to pair with complementary domains of another chain, creating two antigen-binding sites. The diabodies are described more fully, for example, in EP 0 404 097; WO 1993/011161; and Hollinger et al., Proc. Natl. Acad. Sci. USA, 90: 6444-6448 (1993).

As used herein, the linear antibody refers to an antibody that has a pair of tandem Fd fragments (VH-CH1-VH-CH1) forming a pair of antigen binding regions. Linear antibodies may be bispecific or monospecific, as described in Zapata et al., 1995, Protein Eng. 8 (10):1057-1062.

The "domain antibody" is an immune-functional immunoglobulin fragment that contains only the heavy chain variable region or the light chain variable region.

In some cases, two or more VH regions covalently bind with a peptide linker to generate a bivalent domain antibody. The two VH region of the bivalent domain antibody may target the same or different antigens.

The bivalent antibody contains two antigen binding regions. In some cases, the two binding regions have the same antigen specificity. However, the divalent antibody may be bispecific.

The antibody or fragment thereof of the present invention may be generated by methods known in the art, for example, a phage display method or a yeast cell surface expression system. scFv fragments may be prepared by the methods described in U.S. Pat. Nos. 4,946,778 and 5,258,498, and for recombinant production of Fab, Fab', and F(ab')$_2$ fragments, the methods described in WO 1992/022324 or the like may be used.

The antibody of the present invention may be derived from any animals encompassing mammals including humans, birds, and the like. Preferably, the antibody may be an antibody from human, mouse, donkey, sheep, rabbit, goat, guinea pig, camel, horse, or chicken.

The human antibodies have amino acid sequences of human immunoglobulins, and include antibodies isolated from human immunoglobulin libraries or antibodies isolated from animals that are transformed with respect to one or more human immunoglobulins and do not express endogenous immunoglobulins (U.S. Pat. No. 5,939,598).

The antibody of the present invention may be conjugated to enzymes, fluorescent materials, radioactive materials, and proteins, but are not limited thereto. Methods for conjugating the above materials to the antibody have been well known in the art.

The present invention also provides a polynucleotide encoding the antibody or fragment thereof according to an aspect of the present invention as described above.

The polynucleotide may be described as an oligonucleotide or a nucleic acid, and includes DNA molecules (e.g., cDNA or genomic DNA), RNA molecules (e.g., mRNA), DNA or RNA analogues thereof (e.g., peptide nucleic acids and non-naturally occurring nucleotide analogues) produced using nucleotide analogues, and hybrids thereof. The polynucleotide may be single-stranded or double-stranded.

The polynucleotide according to an aspect of the present invention is not particularly limited as long as the polynucleotide encodes the antibody or fragment thereof of the present invention, and preferably, the polynucleotide may include polynucleotides presented by SEQ ID NOs: 7 to 12.

The polynucleotide encoding the antibody or fragment thereof according to an aspect of the present invention may be obtained by the methods known in the art. For example, on the basis of DNA sequences encoding a portion or the entire portions of the heavy and light chains of the antibody or corresponding amino acid sequences, the polynucleotide may be synthesized by oligonucleotide synthesis methods that are known in the art, for example, a polymerase chain reaction (PCR) method.

In addition, the present invention provides a vector containing the polynucleotide.

The vector according to an aspect of the present invention is used for the purpose of replication or expression of the polynucleotide of the present invention for the recombinant production of the antibody or fragment thereof of the present invention, and generally contains one or more of a signal sequence, a replication origin, at least one marker gene, enhancer components, a promoter, and a transcription termination sequence.

The vector of the present invention may be preferably an expression vector, more preferably, one containing a regulatory sequence, for example, a vector containing the polynucleotide sequence of the present invention that is operatively linked to a promoter.

The plasmid, which is a type of vector, means a linear or circular double-stranded DNA molecule to which external polynucleotide fragments can bind. Other forms of vectors may be viral vectors (e.g., replication defective retroviruses, adenoviruses and adeno-associated viruses), and as used herein, additional DNA fragments may be introduced into the viral genomes. Certain vectors are capable of performing autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

The expression vector is a type of vector that can direct the expression of a chosen polynucleotide. One polynucleotide sequence is "operatively linked" to a regulatory sequence if the regulatory sequence affects the expression (e.g., level, timing, or location of expression) of the polynucleotide sequence. The regulatory sequence is a sequence that affects the expression (e.g., level, timing, or location of expression) of the nucleic acid to which it is operatively linked. The regulatory sequence can, for example, exert its effects directly on the regulated nucleic acid, or through the action of one or more other molecules (e.g., polypeptides that bind to the regulatory sequence and/or the nucleic acid). The regulatory sequences include promoters, enhancers, and other expression control elements. The vector according to an aspect of the present invention may be, preferably, the pComb3x (phagemid) vector containing the scFv insert at the SfiI site.

Meanwhile, another aspect of the present invention provides a cell containing the vector according to the present invention.

As used herein, the type of cells according to the present invention is not particularly limited as long as the cells can be used to express the polynucleotide of the present invention.

The cells of the present invention may be host cells, and may be prokaryotes (e.g., *E. coli*), eukaryotes (e.g., yeast or other fungi), plant cells (e.g., tobacco or tomato plant cells), animal cells (e.g., human cells, monkey cells, hamster cells, rat cells, mouse cells, or insect cells) or hybridomas.

The prokaryotes suitable for the purpose of the present invention include gram negative or gram positive organisms, for example, Enterobacteriaceae, such as *Escherichia* (e.g., *E. coli*), *Enterobacter, Erwinia, Klebsiella, Proteus, Salmonella* (e.g., *Salmonella typhimurium*), *Serratia* (e.g., *Serratia marcescens*), and *Shigella*, as well as Bacilli (e.g., *B. subtilis* and *B. licheniformis*), *Pseudomonas* (e.g., *P. aeruginosa*), and *Streptomyces*. The cells of the present invention are not particularly limited as long as they can express the vector of the present invention, but preferably, *E. coli*, for example, *E. coli* ER2537, *E. coli* B, *E. coli* X1776 (ATCC 31,537), *E. coli* W3110 (ATCC 27,325) or *E. coli* capable of expressing LacZ, but are not limited thereto, and more preferably *E. coli* ER2537.

*Saccharomyces cerevisiae* is most frequently used for the eukaryote as the cells of the present invention. However, many other families, species, and strains may be used, such as *Schizosaccharomyces pombe, Kluyveromyces* host, for example, *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; Yarrowia* (EP 402,226); *Pichia pastoris* (EP 183,070); *Candida; Trichoderma reesia* (EP 244,234); *Neurospora crassa; Schwanniomyces*, for example, *Schwanniomyces occidentalis*; and filamentous fungi, for example, *Neurospora, Penicillium, Tolypocladium*, and *Aspergillus* hosts, for example, *A. nidulans* and *A. niger*.

Meanwhile, the cells according to the present invention may be animal cells, especially, vertebrate cells. The proliferation of vertebrate cells in culture (tissue culture) has become a routine procedure, and techniques therefor can be widely used. Examples of the useful mammalian host cells may be monkey kidney CV1 line transformed with SV40 (COS-7, ATCC CRL 1651), human embryonic kidney line (293 or 293 cells subcloned for growth in suspension culture (Graham et al., 1977, J Gen Virol. 36: 59)), baby hamster kidney cells (BHK, ATCC CCL10), Chinese hamster ovary cells/−DHFR (CHO, Urlaub et al., 1980, Proc. Natl. Acad. Sci. USA 77: 4216; e.g., DG44), mouse sertoli cells (TM4, Mather, 1980, Biol. Reprod. 23:243-251), monkey kidney cells (CV1 ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TRI cells (Mather et al., 1982, Annals NY. Acad. Sci. 383: 44-68), MRC 5 cells, FS4 cells, human hepatoma line (Hep G2), human embryonic kidney cell (HER 293 cell), and Expi293F™ cells, but are not limited thereto, and may be preferably CHO cells, human embryonic kidney cells (HER 293 cells) or Expi293F™ cells.

The cells of the present invention are cultured cells that can be transformed or transfected with the polynucleotide of the present invention or the vector containing the same, and subsequently, the polynucleotide or vector may be expressed in the host cells. The recombinant cells refer to cells that are transformed or transfected with a polynucleotide to be expressed. The cells of the present invention contain the polynucleotide of the present invention, but the cells may not express the polynucleotide at a desired level unless the polynucleotide is introduced into the cells such that the regulatory sequence is operatively linked to the polynucleotide.

The cells of the present invention may be cultured in various media. Commercially available media, such as Ham's F10 (Sigma-Aldrich Co., St. Louis, Mo.), minimum essential medium (MEM, Sigma-Aldrich Co.), RPMI-1640 (Sigma-Aldrich Co.), and Dulbecco's modified Eagle's medium (DMEM, Sigma-Aldrich Co.), may be suitable for cell culture. The media may further contain, if necessary, hormones and/or other growth factors, salts, buffers, nucleotides, antibiotics, trace elements, and glucose or equivalent, energy sources.

The medium of the present invention may be preferably SB (Bactotrytone 30 g, yeast extract 20 g, MOPS buffer 10 g/L) Medium, FreeStyle™ 293 Medium, or Expi293™ Medium.

Meanwhile, the present invention provides a method for preparing an antibody or fragment thereof that binds to human KRS, the method comprising:

culturing the above described cells under a condition where a polynucleotide is expressed, thereby preparing a polypeptide comprising light-chain and heavy-chain variable regions; and collecting the polypeptide from the cells or a culture medium in which the cells are cultured.

The cells in the above preparation method are described above, which contain a polynucleotide encoding the antibody according to the present invention.

The polypeptide in the preparation method according to an aspect of the present invention may be the antibody or fragment thereof, per se, of the present invention, and other amino acid sequences, besides the antibody or fragment thereof of the present invention, may be further added to the polypeptide. In these cases, the additionally added amino acids may be removed from the antibody or fragment thereof of the present invention by using methods that are well known to a person skilled in the art.

In the step of culturing, the composition of the medium and the culture conditions may vary depending on the type of cells, and may be appropriately selected and controlled by a person skilled in the art.

The antibody molecules may be accumulated in the cellular cytoplasm, secreted from cells, or targeted into the periplasm or extracellular medium (supernatant) by appropriate signal sequence. Preferably, the antibody molecules are targeted into the periplasm or extracellular medium. In addition, preferably, the produced antibody molecules are refolded by methods that are well known to a person skilled in the art so that the antibody molecules have functional conformations.

The collection of the polypeptide may vary according to the characteristics of the produced polypeptide and characteristics of the cells, and may be appropriately selected and controlled by a person skilled in the art.

The polypeptide may be produced in the intracellular or periplasmic spaces or directly secreted into a medium. If the polypeptide is produced in the cells, the cells may be disrupted to release a protein in a first stage. Particle type debris, host cells, or lysed fragments, are removed by, for example, centrifugation or ultrafiltration. If the antibody is secreted into the medium, the supernatant from the expression system is first concentrated by using a commercially available protein concentration filter, for example, Amicon or Millipore Pellicon ultrafiltration unit. For the inhibition of proteolytic degradation, a protease inhibitor, for example, PMSF, may be contained in any preceding stage, and in order to prevent the unexpected growth of contaminants, antibiotics may be contained.

Antibodies prepared from cells may be purified by using, for example, hydroxyapatite chromatography, gel electrophoresis, dialysis, and affinity chromatography, while the antibody according to an aspect of the present invention may be preferably purified through affinity chromatography.

The antibody or fragment thereof of the present invention specifically binds to KRS, and thus is useful in the diagnostic analysis for detecting or quantifying the KRS protein, for instance, detecting the KRS expression in particular cells, tissues, or serum.

Therefore, the present invention provides a KRS-specific detection method comprising: bringing the antibody or fragment thereof according to an aspect of the present invention into contact with a sample; and detecting the antibody or fragment thereof.

In order to "detect" the antibody or fragment thereof, the antibody or fragment thereof may be generally labeled with a detectable moiety.

For example, the antibody or fragment thereof may be labeled with radioisotopes or fluorescent labels using the technique described in Current Protocols in Immunology, Volumes 1 and 2, 1991, Coligen et al., Ed. Wiley-Interscience, New York, N.Y., Pubs. Radioactivity may be measured by, for example, scintillation counting, and the fluorescence may be quantified using a fluorometer.

In addition, various enzyme-substrate labels may be utilized. Exemplary enzymatic labels include luciferase (such as drosophila luciferase and bacterial luciferase (U.S. Pat. No. 4,737,456)), luciferin, 2,3-dihydrophthalazinediones, malate dehydrogenase, urase, peroxidase (such as horseradish peroxidase (HRPO)), alkaline phosphatase, β-galactosidase, glucoamylase, lysozyme, saccharide oxidase (e.g., glucose oxidase, galactose oxidase, and glucose-6-phosphate dehydrogenase), heterocyclic oxidase (e.g., uricase and xanthine oxidase), lactoperoxidase, microperoxidase, and the like. The conjugation of the enzyme to the antibody is preferably described in O'Sullivan et al., 1981, Methods for the Preparation of Enzyme-antibody Conjugates for use in Enzyme Immunoassay, in Methods in Enzyme (J. Langone & H. Van Vunakis, eds.), Academic press, N. Y., 73: 147-166).

The labels may be indirectly conjugated to antibodies using various known techniques. For example, the antibody may be conjugated to biotin, and any labels pertaining to three classes of widespread categories cited above may be conjugated to avidin or vice versa. Biotin may selectively bind to avidin, and therefore, this label may be conjugated to the antibody in such an indirect manner. Alternatively, in order to attain the indirect conjugation of a label to an antibody, the antibody may be conjugated to small hapten (e.g., digoxin), and one of different types of labels recited above may be conjugated to the anti-hapten antibody (e.g., anti-digoxin antibody). Therefore, the indirect conjugation of the label to the antibody can be attained.

The antibody or fragment thereof of the present invention may be used by any known analysis method, such as competitive binding analysis, direct and indirect sandwich analysis, and immunoprecipitation analysis.

The antibody or fragment thereof of the present invention may be used for a diagnostic kit, that is, a diagnostic kit for performing diagnostic analysis, which is a combination of reagents packaged in predetermined amounts together with the operation manual. If the antibody is labeled with an enzyme, the kit may contain a substrate and a cofactor as a substrate precursor providing a chromophore or a fluorophore, which is required by the enzyme. The kit may also contain other additives, such as a stabilizer, a buffer (e.g., block buffer or lysis buffer). The relative amounts of various reagents may be widely varied in order to provide the concentrations of the reagents in a solution to sufficiently optimize the sensitivity of analysis. The reagents may be provided as a generally freeze-dried or dried powder, including a vehicle, by which a reagent solution having an appropriate concentration is provided when the reagents are dissolved.

It has been revealed that if KRS, which is detected by the antibody according to an aspect of the present invention, is promoted to be secreted out of cells by TNF-α, the secreted KRS binds to and activates macrophage cells, thereby inducing an immune response. It has been reported that the bound KRS increases the TNF-α-induced activity of the macrophage cells or the cellular migration through signaling by p38 mitogen activated kinase or the like (Park, S. G., et al Kim, H. J., Min, Y. H., Choi, E. C., Shin, Y. K., Park, B. J., Lee, S. W. and Kim, S. 2005 Human lysyl-tRNA synthetase is secreted to trigger proinflammatory response 2005 Proc. Natl. Acad. Sci. 102(18), 6356-6361). Also, KRS has been recently revealed to be involved in various diseases. It has been reported that autoantibodies to KRS are present in inflammatory muscle disease patients (Gelpi, C., Kanterewicz, E., Gratacos, J., Targoff, I. N. & Rodriguez-Sanchez, J. L. Coexistence of two anti-synthetases in a patient with the anti-synthetase syndrome (1996) Arthritis Rheum. 39, 692-697); and KRS is involved in Lou Gehrig's disease by binding to SOD1 in patients with SOD1 gene mutation causing Lou Gehrig's disease (Kunst, C. B., Mezey, E., Brownstein, M. J. & Patterson, D. Mutations in SOD1 associated with amyotrophic lateral sclerosis cause novel protein interactions (1997) Nat. Genet. 15, 91-94). In addition, it has been recently reported that the phosphorylated KRS in cancer cells contributes to the stabilization of Laminin receptors to promote the metastasis of cancer cells (Kim, D G et al Chemical inhibition of prometastatic lysyl-tRNA synthetase laminin receptor interaction (2013) Nat Chem. Biol.).

Therefore, the KRS may be used as a diagnostic marker for diagnosing particular cancers, autoimmune diseases or inflammatory diseases, and evaluating progression states of the diseases and prognosis before or after therapy, through KRS detection. The diagnosis of cancers, autoimmune diseases or inflammatory diseases, or the evaluation of prognosis thereof according to the present invention, may be carried out by detecting the KRS protein in biological samples.

Therefore, the present invention provides a composition for diagnosing cancer comprising the antibody or fragment thereof according to an aspect of the present invention as an active ingredient. The present invention also provides a composition for diagnosing an autoimmune disease comprising the antibody or fragment thereof according to an aspect of the present invention as an active ingredient. The present invention also provides a composition for diagnosing an inflammatory disease comprising the antibody or fragment thereof according to an aspect of the present invention as an active ingredient.

Therefore, the present invention provides a use of the antibody or fragment thereof according to an aspect of the present invention for preparing an agent for cancer diagnosis. The present invention also provides a use of the antibody or fragment thereof according to an aspect of the present invention for preparing an agent for autoimmune disease diagnosis. The present invention also provides a use of the antibody or fragment thereof according to an aspect of the present invention for preparing an agent for inflammatory disease diagnosis.

Therefore, the present invention provides a method for diagnosing cancer, an autoimmune disease, or an inflammatory disease, the method comprising: (a) obtaining a biological sample from a subject; (b) determining the level of KRS protein in the biological sample using the antibody or fragment thereof according to an aspect of the present invention; and (c) comparing the determined level of KRS protein with the level of KRS protein in a normal subject.

The biological sample includes blood and other liquid samples having biological origins, biopsy samples, solid tissue samples such as tissue culture, or cells derived therefrom. More specifically, examples of the biological sample may include, but are not limited to, tissues, extracts, cell lysates, whole blood, plasma, serum, saliva, ocular fluid, cerebrospinal fluid, sweat, urine, milk, ascites fluid, synovial fluid, peritoneal fluid, and the like. The sample may be obtained from animals, preferably mammals, and most preferably humans. The sample may be pre-treated before its use for detection. For example, the sample may be pre-treated by filtration, distillation, extraction, concentration, inactivation of interference components, reagent addition, and the like. In addition, nucleic acid and proteins isolated from the sample may be used for detection.

The detection is described as above.

According to the diagnosis method of the present invention, the actual occurrence of the disease can be diagnosed by comparing the KRS protein level in a biological sample of a normal subject and the KRS protein expression level in a biological sample of a subject with suspected cancer, autoimmune disease, or inflammatory disease. That is, the KRS protein level from a biological sample with suspected cancer, autoimmune disease, or inflammatory disease is measured by using the antibody or fragment thereof of the present invention, and the KRS protein level from a biological sample of a normal subject is measured by using the antibody or fragment thereof of the present invention, followed by a comparison between the measured levels of the KRS protein, and then if the expression level of the KRS protein of the subject with suspected disease is higher than that of the normal subject, the subject may be diagnosed to have the corresponding disease.

Examples of the cancer may include, but are not particularly limited to, breast cancer, large intestine cancer, lung cancer, small cell lung cancer, gastric cancer, liver cancer, blood cancer, bone cancer, pancreatic cancer, skin cancer, head or neck cancer, cutaneous or intraocular melanoma, uterine cancer, ovarian cancer, rectal cancer, anal cancer, colon cancer, fallopian tube carcinoma, endometrial carcinoma, cervical cancer, vaginal cancer, vulvar carcinoma, Hodgkin's disease, esophageal cancer, small intestine cancer, endocrine cancer, thyroid cancer, parathyroid carcinoma, adrenal cancer, soft tissue sarcoma, urethral cancer, penile cancer, prostate cancer, chronic or acute leukemia, lymphocyte lymphoma, bladder cancer, kidney or ureter cancer, renal cell carcinoma, renal pelvic carcinoma, CNS tumor, primary CNS lymphoma, spinal cord tumor, brain stem glioma, and pituitary adenoma, and may be preferably carcinomas that act upon laminin receptors to promote metastasis, for example, lung cancer or pancreatic cancer.

Examples of the autoimmune diseases may be selected from the group consisting of Crohn's disease, erythema, atopy, rheumatoid arthritis, Hashimoto's thyroiditis, pernicious anemia, Addison's disease, Type 1 diabetes, Lou Gehrig's disease, inflammatory muscle disease (e.g., polymyositis or dermatomyositis), lupus, chronic fatigue syndrome, fibromyalgia, hypothyroidism and hyperthyroidism, scleroderma, Behcet's disease, inflammatory bowel disease, multiple sclerosis, myasthenia gravis, Meniere's syndrome, Guillain-Barre syndrome, Sjogren's syndrome, vitiligo, endometriosis, psoriasis, leukoplakia, systemic scleroderma, asthma, ulcerative colitis, or the like. Preferably, the autoimmune disease may be rheumatoid arthritis, Lou Gehrig's disease, polymyositis, or dermatomyositis.

Examples of the inflammatory disease may include, but are not limited to, in addition to common inflammation such as edema, inflammatory bowel disease, peritonitis, osteomyelitis, cellulitis, pancreatitis, trauma-induced shock, bronchial asthma, allergic rhinitis, cystic fibrosis, acute bronchitis, chronic bronchitis, acute bronchiolitis, chronic bronchiolitis, osteoarthritis, gout, spondyloarthropathy, ankylosing spondylitis, Reiter's syndrome, psoriatic arthropathy, spondylitis associated with inflammatory bowel disease, juvenile arthropathy, juvenile ankylosing spondylitis, reactive arthropathy, infectious arthritis, post-infectious arthritis, gonococcal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Lou Gehrig's granulomatosis, polymyalgia rheumatica, joint cell arteritis, calcium pyrophosphate deposition arthropathy, pseudo gout, non-articular rheumatism, bursitis, tendovaginitis, epicondylitis (tennis elbow), neuropathic joint disease (or called "charcot joint"), hemarthrosis, Henoch-Schönlein purpura, hypertrophic osteoarthropathy, multicentric reticulohistiocytoma, scoliosis, hemochromatosis, hemoglobinopathy, hyperlipoproteinema, hypogammaglobulinemia, familial Mediterranean fever, Behat's disease, systemic lupus erythematosus, relapsing fever, multiple sclerosis, septicemia, septic shock, acute respiratory distress syndrome, multiorgan dysfunction syndrome, chronic obstructive pulmonary disease, rheumatoid arthritis, acute lung injury, bronchopulmonary dysplasia, Type 2 diabetes, arteriosclerosis, Alzheimer's dementia, familial cold autoinflammatory syndrome, Muckle-Wells syndrome, neonatal mutisystem inflammatory disease, chronic infantile neurologic cutaneous articular syndrome, adult-onset Still's disease, contact dermatitis, hydatidiform mole, syndrome of pyogenic arthritis, pyoderma gangrenosum, and acne (PAPA), hyperimmunoglobulin D syndrome, and cryopyrin-associated periodic syndromes.

The method for diagnosing cancer, autoimmune disease, and inflammatory disease can be attained through an antibody-antigen response between the anti-KRS antibody or fragment thereof of the present invention and the KRS protein specifically binding thereto. As used herein, the term "antigen-antibody complex" refers to KRS, which is a marker for cancer, autoimmune disease, and inflammatory disease, and the anti-KRS antibody specifically binding thereto, of the present invention. The amount of the antigen-antibody complex formed may be quantitatively measured through the intensity of the signal of the detection label.

Examples of the detection label may be selected from the group consisting of enzymes, fluorescent materials, ligands, luminescent materials, microparticles, redox molecules, and radioisotopes, but are not limited thereto. When the enzyme is used as the detection label, examples of the usable enzyme may be β-glucuronidase, β-D-glucosidase, β-D-galactosidase, urease, peroxidase or alkaline phosphatase, acetylcholine esterase, glucose oxidase, hexokinase and GDPase, RNase, glucose oxidase, luciferase, phospho-fructokinase, phosphoenolpyruvate, carboxylase, aspartate amino transferase, phosphenol pyruvate decarboxylase, β-lamatase, or the like, but are not limited thereto. Examples of the fluorescent material may be fluorescein, isothiocyanate, rhodamine, phycoerythrin, phycocyanin, allophycocyanin, o-phthaldehyde, fluorescamin, or the like, but are not limited thereto. Examples of the ligand may be biotin derivatives or the like, but not limited thereto. Examples of the luminescent material may be acridinium ester, luciferin, luciferase, or the like, but are not limited thereto. Examples of the microparticles may be colloidal gold, colored latex, or the like, but are not limited thereto. Examples of the redox molecule may be ferrocene, ruthenium complexes, viologen, quinone, Ti ions, Cs ions, diimide, 1,4-benzoquinone, hydroquinone, $K_4W(CN)_8$, $[Os(bpy)_3]^{2+}$, $[RU(bpy)_3]^{2+}$, $[MO(CN)_8]^{4}$, or the like, but are not limited thereto. Examples of the radioisotope may be $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, $^{186}Re$, or the like, but are not limited thereto.

In an example of the present invention, the library was constructed by using the human VH3-23/VL1g gene as a frame and inserting random sequences into CDRs, and then antibodies were isolated by selecting phages selectively binding to KRS, followed by purification and sequencing.

In another example of the present invention, the binding of the purified antibodies to KRS was investigated by the western blot method. As a result, the antibody of the present invention was verified to bind with KRS.

In still another example of the present invention, the affinity of the anti-KRS scFV antibody of the present invention to KRS was determined by surface resonance analysis. As a result, it was verified that the antibody of the present invention had an equilibrium dissociation constant of 100 nM, indicating its relatively high affinity.

In another example of the present invention, the cross activity of the anti-KRS scFv antibody of the present invention was measured. As a result of measuring reactivity of the antibody of the present invention and eight types of similar proteins including KRS using Luminex beads, it was verified that the antibody of the present invention did not bind to the other types of ARS proteins except for KRS.

In still further another example of the present invention, the effectiveness of the anti-KRS scFv antibody of the present invention as a diagnostic antibody was tested. A plate coated with the antibody of the present invention was manufactured, and then allowed to react with the KRS standard material for different concentrations through dilution, and then the binding therebetween was measured through ELISA. As a result, it was verified that the binding of the antibody to the KRS standard material was measured in a concentration-dependent manner, and the antibody of the present invention can be used for the diagnosis of cancer, autoimmune disease or inflammatory disease.

In still another example of the present invention, the blood of a patient with pancreatic cancer was analyzed by an ELISA kit developed using the anti-KRS antibody of the present invention. As a result, it was verified that KRS was expressed at an equivalent degree to CA19-9, which is the most representative biomarker of pancreatic cancer, and thus it was verified that KRS can be used as a biomarker for cancer diagnosis, and thus the antibody of the present invention is useful.

In addition, for comparative analysis of KRS with several other biomarker candidates of pancreatic cancer, the other biomarker candidates were comprehensively compared and analyzed using the multiplex bead assay kit. As a result, it was verified that KRS can be used as a representative cancer biomarker together with CA 19-9, compared with the other available biomarkers, and the antibody of the present invention is useful.

Advantageous Effects

Therefore, the antibody or fragment thereof according to the present invention specifically binds to human KRS and has no cross activity with other proteins including the same ARS family, thereby enabling KRS detection and inhibition, and thus the antibody or fragment thereof according to the present invention is effective in the detection of KRS and the diagnosis of cancer or autoimmune disease and inflammatory disease, which are diseases in association with KRS.

BRIEF DESCRIPTION OF THE DRAWINGS

FIG. 3 illustrates a graph showing cross activity results of the antibody of the present invention, anti-KRS scFv Biocon-K1, measured by Luminex Multiplex Assay (Vertical axis (FI): fluorescent intensity, WRS: tryptophanyl-tRNA synthetase, HRS: histidyl-tRNA synthetase, NRS: asparaginyl-tRNA synthetase, KRS: lysyl-tRNA synthetase, SRS: seryl-tRNA synthetase, YRS: tyrosyl-tRNA synthetase, GRS: glycyl-tRNA synthetase, AIMP1: aminoacyl-tRNA-synthetase-interacting multifunctional protein 1).

MODE FOR CARRYING OUT THE INVENTION

Figure 1:
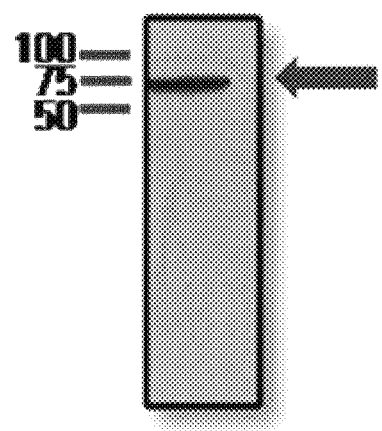
FIG. 1 illustrates western blot test results investigating whether the antibody of the present invention binds to a target protein, i.e. KRS.

Hereinafter, the present invention will be described in detail with reference to the following examples.

However, the following examples are merely for illustrating the present invention and are not intended to limit the scope of the present invention.

Example 1 scFv Library Construction and Anti-KRS scFv Section

<1-1> scFv Library Construction

The scFv library was constructed by the method disclosed in Korean Patent No. 10-0961392.

The library was designed such that human VH3-23/VL 1 g gene was used as a frame and random sequences were inserted into complementarity determining regions (CDRs), and then a pFDV plasmid vector was produced by introducing restriction enzyme cleavage sequences immediately after reader sequences of the β-lactamase gene in the plasmid vector having the β-lactamase gene as a selective marker, followed by insertion of scFv gene library, transfection in *E. coli*, and culturing, thereby constructing the library. Through this procedure, most of scFv gene sequences having abnormal stop codons or frameshifts were removed from the library, thereby improving the quality of the library. The error-removed sequences were amplified through a polymerase chain reaction from the cultured library, and the scFv gene library recombined therefrom was inserted into pComb3X phagemid vector, and *E. coli* ER2537 strain was transfected with the vector, thereby obtaining a final library. The library was cultured in 400 ml of super broth (SB) medium containing carbenicillin, and when the absorbance at 600 nm was 0.5, $10^{13}$ CFU of VCSM13 auxiliary phages were applied thereto, followed by stirring at 80 rpm and infection at 37° C. for 1 hour. Then, a final concentration of 70 µg/ml kanamycin antibiotic were put thereto, followed by culturing overnight with stirring at 200 rpm at 30° C., thereby producing phages with scFv represented on a surface thereof. The next day morning, the culture liquid was centrifuged, and the phages in the culture liquid were precipitated by adding 4% polyethylene glycol-800 and 3% sodium chloride. The precipitated phages were dissolved in 50 ml of PBS buffer, and again precipitated in the above manner, thereby finally dissolving the phages in 2 ml of PBS buffer. Foreign materials were removed through centrifugation, thereby obtaining the phage scFv library. Generally, the final phage library contains $10^{13}$ CFU/ml or more of phage particles.

<1-2> Anti-KRS scFv Selection

10 µg/ml KRS was added to an immunotube to allow the protein to adhere to a surface of the tube for 1 hour, and then a 3% powdered milk solution was added to the tube to protect the KRS-non-adhering surface portion. After the tube was evacuated, $10^{12}$ CFU of antibody phage library dispersed in a 3% powdered milk solution was added to the tube to bind to the antigen. Non-specifically bound phages were washed out three times with TBST (tris buffered saline—Tween 20) solution, and then the remaining antigen-specific phage antibody was eluted using 100 mM triethylamine solution.

The eluted phages were neutralized with 1.0 M Tris-HCl buffer (pH 7.8), and then infected into *E. coli* ER2537 at 37° C. for 1 hour, and the infected *E. coli* cells were plated on carbenicillin-containing LB (Luria-Bertani) agar medium, followed by culturing at 37° C. On the next day, the cultured *E. coli* cells were suspended in 3 ml of SB (super broth)-carbenicillin culture medium, and 15% glycerol was added thereto. A portion of the suspension was stored at −80° C., and 50 µl of the remainder was inoculated in 20 ml of SB-carbenicillin-2% glucose solution, followed by culturing at 37° C. When the absorbance of the culture liquid reached 0.5 at 600 nm, the culture liquid was centrifuged to separate only bacteria, and the remaining material was suspended again in 20 ml of SB-carbenicillin medium, and $10^{12}$ PFU (plaque formation unit) of VCSM13 helper phages were added thereto, followed by culturing at 37° C. with slow stirring.

After 1 hour, 70 µg/ml kanamycin was added, followed by culturing at 30° C. overnight with fast stirring (250 rpm). On the next day, the culture liquid was centrifuged, and then the above panning process was repeated using, as a library, 1 ml of the supernatant containing phage particles, thereby concentrating antigen-specific clones.

Example 2

Anti-KRS scFv Antibody Expression and Purification

After three or four runs of repetitive panning, *E. coli* containing antibody genes were coated and incubated on carbenicillin-containing LB agar medium to obtain single colonies, which were then inoculated and incubated in 200 µl of SB-carbenicillin solution, and then the expression of scFv protein in the periplasm of *E. coli* was induced by IPTG. The *E. coli* cells were suspended in 40 µl of 1×TES (50 mM Tris, 1 mM EDTA, 20% Sucrose, pH 8.0), and then 60 µl of 0.2×TES solution was added thereto, followed by standing at 4° C. for 30 minutes or more. Then, the suspension was centrifuged to extract the periplasm into the supernatant.

<2-1> Expression of scFv Antibody Selected for KRS

The selected scFv positive single-colony clones for KRS were incubated in 5 ml of carbenicillin-containing SB medium (Bactotrytone 30 g, yeast extract 20 g, MOPS buffer 10 g/L) to start seed culture, and after the culturing overnight, the culture liquid was transferred to 500 ml of carbenicillin-containing SR medium. When the OD value at 600 nm reached about 0.5, IPTG was added to 1 mM, followed by culturing at 30° C. overnight, thereby expressing scFv protein in the periplasm of *E. coli*. On the next day, the *E. coli* cells obtained through centrifugation were suspended in 1×TES buffer (50 mM Tris, 1 mM EDTA, 20% Sucrose, pH 8.0), and then 0.2×TES was added at 1.5 fold, followed by mixing. The suspension was centrifuged to extract the periplasm.

<2-2> Purification of Selected scFv Antibody 5 mM (final) MgSO4 was added to the scFv antibody extracted from the periplasm, and the resultant material was mixed with Ni-NTA beads that were in advance equilibrated with PBS, followed by stirring for 1 hour in a cold storage to allow the antibody to bind to the Ni-beads. Thereafter, affinity chromatography was conducted to sufficiently wash the non-bound proteins using BPS. After further sufficient washing with buffer containing 5 mM Imidazole, the bound scFv antibody was eluted using 200 mM imidazole buffer. The eluted antibody was dialyzed, and the purity thereof was checked by electrophoresis. The protein was quantified by BCA assay, and the amount of purified antibody was recorded, and then a constant amount of antibody was dispensed and then frozen-stored.

<2-3> Immunoblotting and Sequencing

The scFv antibody extracted from the periplasm was used to investigate whether the scFv antibody binds to KRS originally expressed in human cells, by using western blot assay. 50 µg of Hela cell lysate was electrophoresed through SDS PAGE, transferred to the nitrocellulose membrane by a wet transfer method, and blocked with 3% skim milk, and then the extracted scFv antibody was added to bind thereto. For detection, the horseradish peroxidase (HRP)-conjugated anti-HA secondary antibody was allowed to react with the bound scFv antibody, and the film was photosensitized in dark room using ECL reagent as a substrate. The photosensitized bands were compared with standard molecule markers to confirm bands corresponding to the KRS size.

Antigen-specific antibody clones confirmed therefrom were incubated in 10 ml of carbenicillin-containing SR medium overnight. The plasma DNA was extracted using the plasmid miniprep kit, and sequenced through capillary sequencing service (Macrogen Co). CDR sequences were analyzed on the basis of Kabat protein sequence database and the international ImMunoGeneTics information system (IMGT) analysis.

As a result, the number of scFv fragments binding to KRS antigen is a total of one, and the nucleotide sequence thereof was confirmed to have SEQ ID NO: 14.

Example 3

Measurement of Affinity of Anti-KRS scFv Antibody

The binding affinity of the antibody of the present invention to KRS antigen was measured using the ProteOnT-MXPR36 SPR (surface plasmon resonance) biosensor (Bio-Rad).

Specifically, approximately 10 μg/ml KRS antigen was immobilized at about 2,000-4,000 response units to GLC chip (Bio-Rad 6×6 sensor chip, Compact capacity amine coupling for protein-protein interactions) according to the manufacturer's manual, and then 30 μl of the purified scFv antibody of the present invention, which was diluted with PBS to various concentrations (500-30 nM), was injected to the chip at a rate of 50 μl/min at 25° C. to quantify the interaction with the antigen. The surface of the chip was regenerated with 0.85% phosphoric acid. The association rate and dissociation rate were calculated using the ProteOn Manager software, and the equilibrium dissociation constant (KD) was calculated as a ratio of dissociation rate/association rate.

Figure 2:
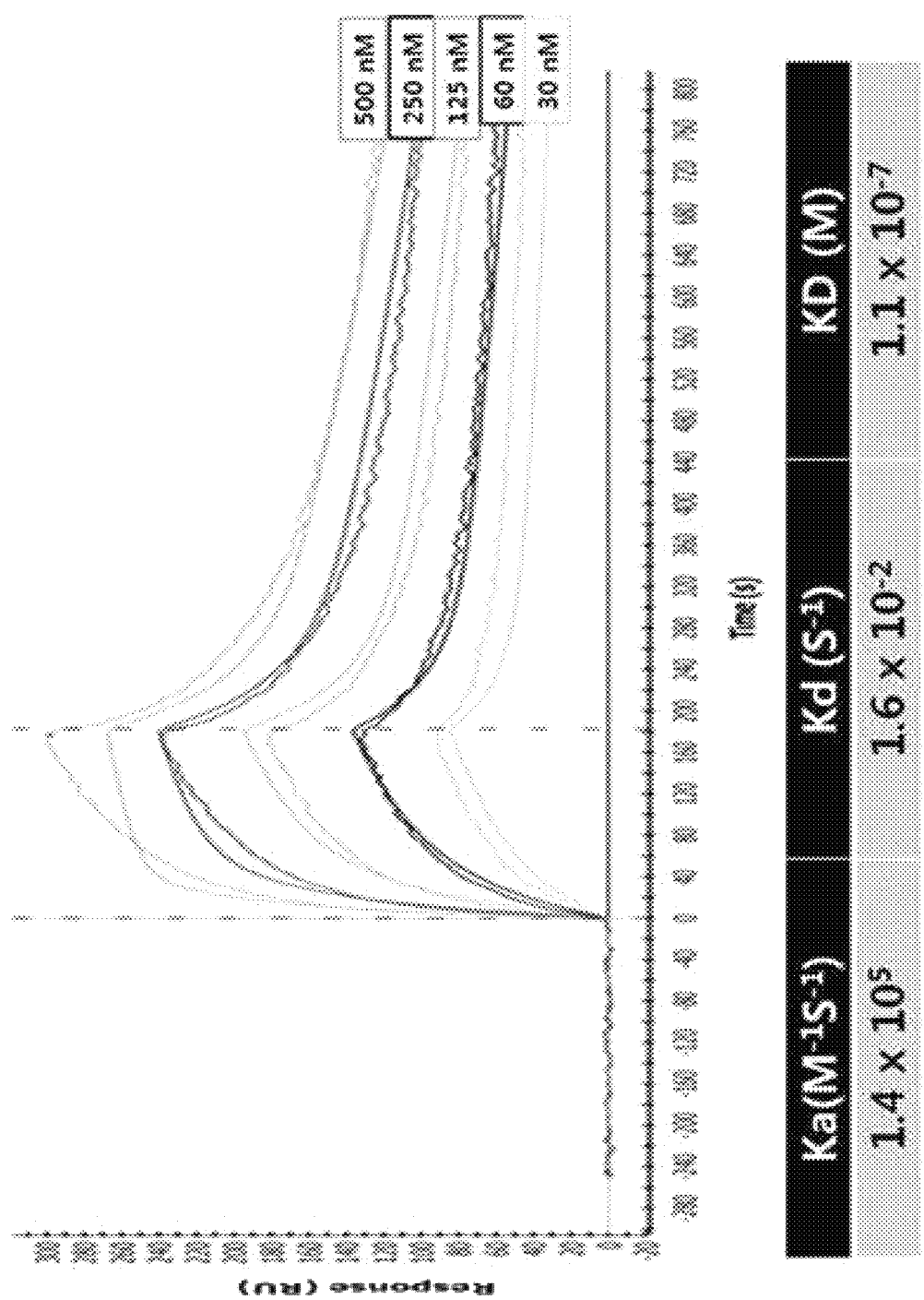
FIG. 2 illustrates a graph showing binding affinity of the antibody of the present invention, i.e. anti-KRS scFv Biocon-K1, measured by surface plasmon resonance (SPR) (Kd: equilibrium dissociation constant, horizontal axis: time (sec), vertical axis: response unit (RU)).

As shown in FIG. 2, the results verified that the antibody of the present invention had the maximum KD value of 100 nM, indicating relatively high affinity to KRS.

Example 4

Measurement of Cross Activity of Anti-KRS scFv Antibody

In order to determine whether the scFv antibody has reactivity with other antigens, the cross activity of the antibody of the present invention with KRS and other ARS family proteins was measured using Luminex beads.

<4-1> Manufacturing of Luminex Beads Having Respective Proteins Conjugated Thereto In order to bind amine residues of proteins to beads with different code numbers, respectively, coupling was performed according to the test procedure for Amine coupling kit from Bio-Rad. First, respective beads corresponding to 1×10⁶ were transferred to a 96-well filter plate, and washed with an activation buffer using a vacuum manifold. Then, 50 mg/ml S—NHS (N-hydroxysulfosuccinimide) and 50 mg/ml EDAC (1-ethyl-3-[3-dimethylaminopropyl]carbodiimide) were added, followed by activation at room temperature for 20 minutes. The activated beads were washed with PBS, and then 10 μg of respective recombinant ARS antigens, that is, WRS, HRS, NRS, KRS, SRS, YRS, GRS, and AIMP1(p43), which were purified at purity of 90% or higher, were added, followed by reaction at room temperature for 2 hours. The beads linked to the respective ARS antigens were washed. two times with PBS, and then a blocking buffer was added to perform a reaction at room temperature for 30 minutes, thereby blocking unbound residues. Then, the resultant beads were washed two times with PBS, and again dispersed in 100 μl of PBS, and kept in tubes in which the light was blocked. The number of beads bound was measured and recorded by hemocytometer.

<4-2> Measurement of Cross Activity using Multiplex Assay

The antibody of the present invention extracted from the periplasm was first diluted with a specimen diluent (PBST+ 2% BSA) to 1:400. Then, the diluted antibody was diluted 2-fold serially with a specimen diluent, and dispensed in 96 well filter plate at 50 μl for each well. Only the specimen diluent was added in the blank well without the antibody. The ARS-bound beads were put in bead mix tubes to 2000 beads per well, respectively, and the specimen diluent was put with a volume such that 50 μl of the specimen diluent could be put per well. The bead mix solution was well mixed and dispensed in each well, followed by reaction in dark room for 1 hour. After the reaction was ended, the resultant solution was washed three times with PBS (200 μl/well) using a vacuum manifold, 50 μl Anti-(HA)-biotin secondary antibody was added, followed by further reaction in dark room for 1 hour. The beads binding to the secondary antibody were washed three times with PBS, and then, for fluorescent labeling, SA-PE (Streptavidin-Phycoerythrin) was added to 2 μg/ml, followed by reaction in dark room for 30 minutes, washing three times with PBS, and again dispersion in 100 μl of PBS. The fluorescent intensity of the fluorescence-labeled beads was measured using Bio-Plex (Luminex) 200 equipment and Bio-Plex manager program, and the measurement values were analyzed to investigate the binding of the antibody to each ARS.

Figure 3:
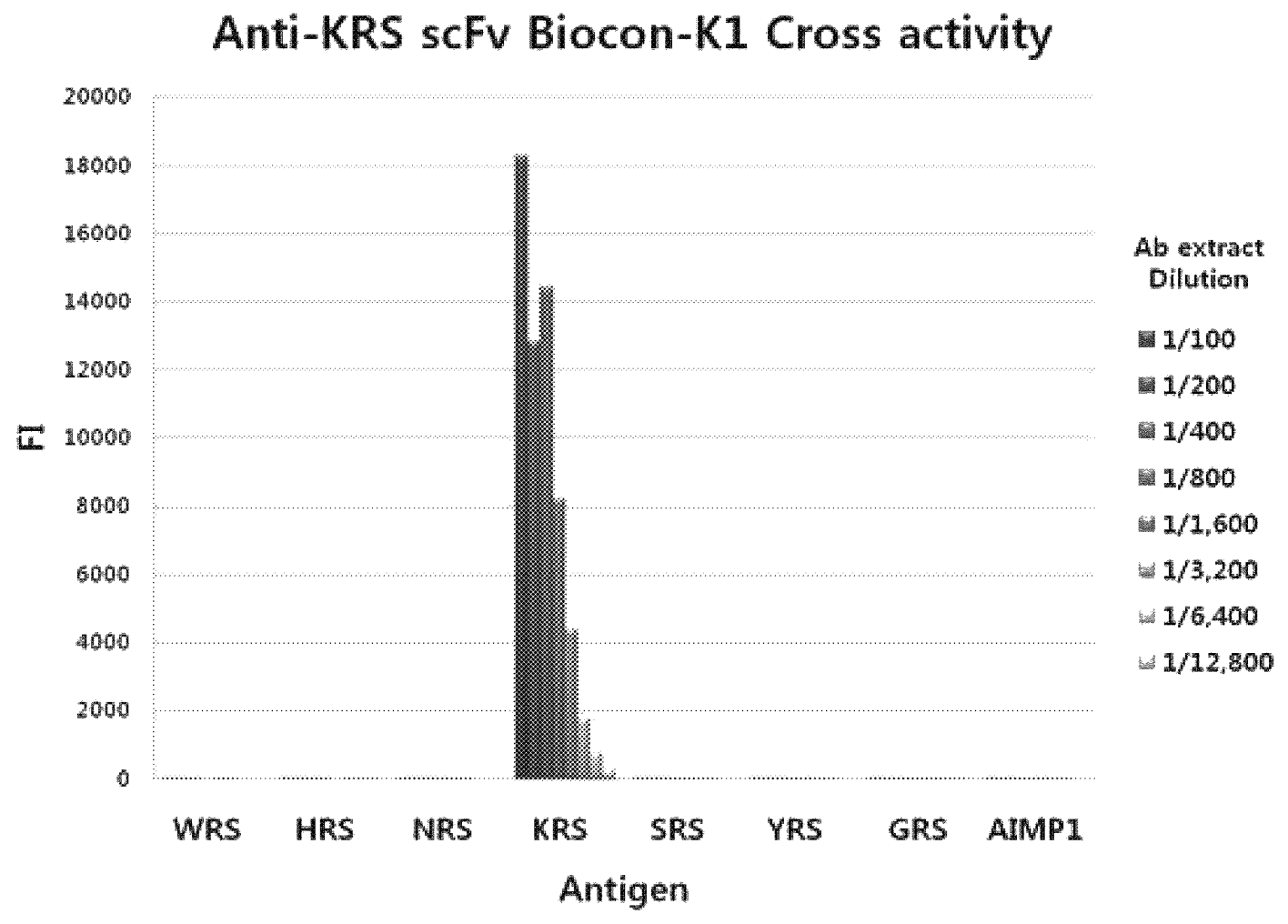

As shown in FIG. 3, the results verified that the antibody of the present invention did not react with other ARS family proteins, except for KRS, at all concentrations.

Therefore, it was confirmed that the antibody of the present invention had no cross activity with other proteins.

Example 5

Sandwich ELISA Pairing Test using Purified Anti-KRS scFv Antibody

In order to investigate the usefulness of the antibody of the present invention as a diagnostic antibody, KRS sandwich ELISA pairing test was performed. It was investigated whether the quantitative curve with respect to a KRS standard material was made by performing a pairing test using the antibody of the present invention as a capture antibody and using the rabbit polyclonal antibody of the existing product as a detection antibody, among components of ELISA.

First, the purified antibody of the present invention was diluted with a coating buffer (0.1 M sodium carbonate pH 9.0), and 100 μl of the diluted antibody was dispensed in the ELISA plate to 100-400 ng per well, followed by standing at room temperature for 3 hours. The reaction material was washed three times with PBST, and 350 μl of BSA (2%)— containing PBST was added to perform blocking at room temperature for 1 hour, followed by washing three times with PBST. The purified recombinant KRS standard material was 2-fold serially diluted with a specimen diluent for different concentrations, and then 100 μl of the KRS standard material was put in each plate well coated with the antibody, followed by reaction at room temperature for 1 hour. After the reaction, the plate was washed three times with PBST, 100 μl of the diluted detection antibody (4

μg/ml) was added, followed by reaction at room temperature for 1 hour. For detection, the plate was washed three times with PBST, and HRP-linked anti-rabbit IgG was put in the plate, followed by reaction at room temperature for 1 hour. In order to investigate the chromic reaction by HRP, the plate was washed three times with PBST, and 50 μl of TMB solution as an HRP substrate was added to monitor the chromic reaction for 10 minutes. Thereafter, 50 μl of 2 N sulfuric acid was added to stop the chromic reaction, and then the absorbance at 450 nm was measured using ELISA reader.

Figure 4:
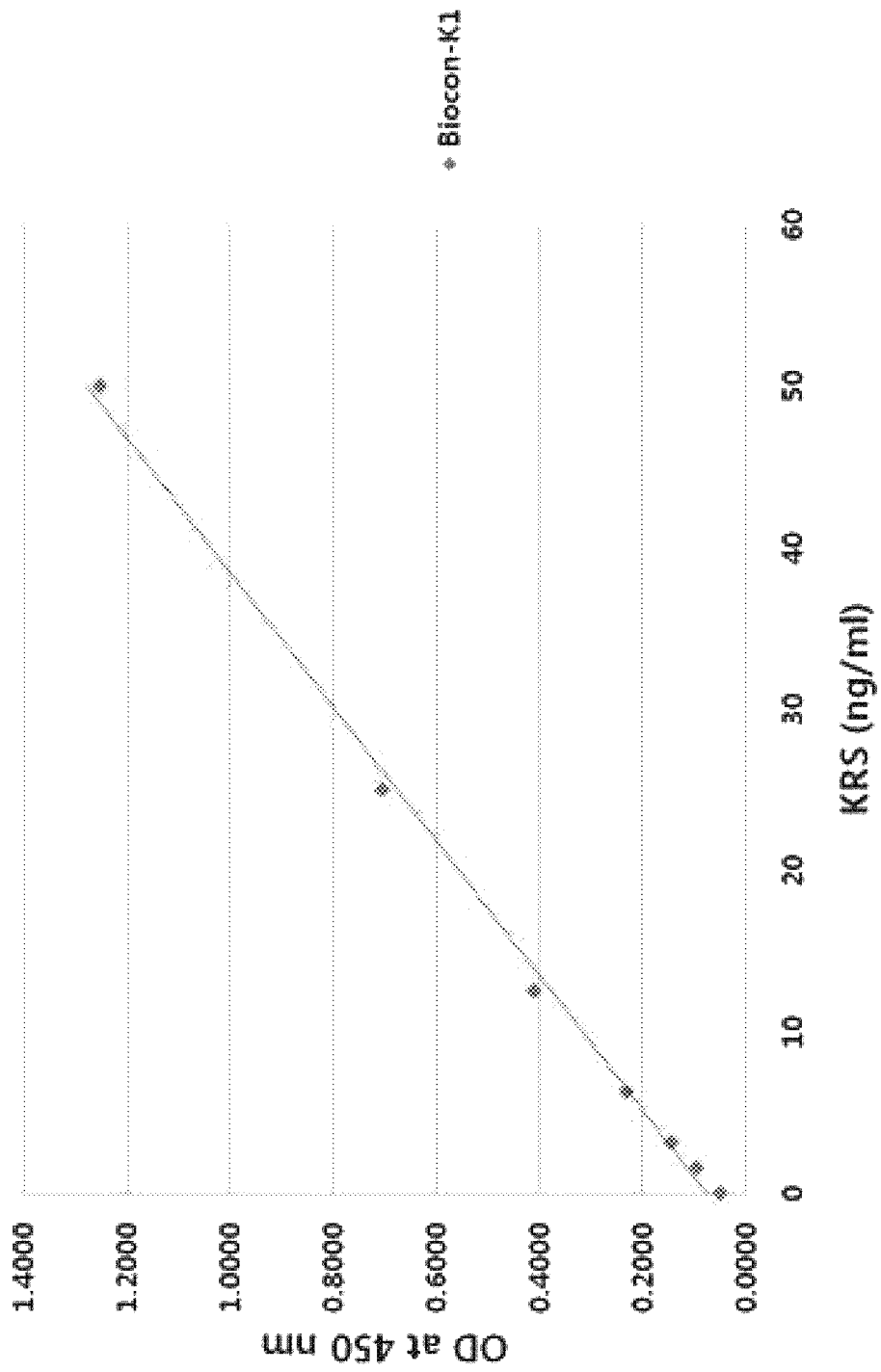
FIG. 4 illustrates ELISA test results for investigating whether the antibody of the present invention can detect KRS (vertical axis: 450 nm absorbance, horizontal axis: KRS standard material concentration (ng/ml)).

As shown in FIG. 4, the results verified that the standard line corresponding to the ng/ml concentration for the recombinant KRS standard material was drawn. Therefore, it was confirmed that the antibody of the present invention can be used for cancer diagnosis.

Example 6

Comparative Analysis of Blood KRS Biomarker of Pancreatic Cancer Patients Using Anti-KRS Antibody The ELISA kit product for search has been developed using the newly developed KRS antibody. In order to validate the usefulness of the blood KRS protein as a biomarker for pancreatic cancer using the kit product and investigate whether the developed ELISA kit can be used in the measurement of the biomarker in the serums of patients, the serums of normal persons and pancreatic cancer patients were received and used for the test.

Test was conducted by using the serums of normal persons (N=8) and pancreatic cancer patients (N=16) that were received from Kyungpook National University Hospital and passed through IRB deliberation from Korea Biobank Network of Korea Centers for Disease Control and Prevention. In order to validate the usefulness of the blood KRS protein as a biomarker for pancreatic cancer, the test was performed by comparison with the blood concentration of CA19-9 as an existing pancreatic cancer biomarker.

The KRS ELISA kit trial product developed by the present applicant and the CA19-9 ELISA on the market were used according to the manufacturer's indications. Specifically, a specimen diluent was added to the 96-well plate coated with the antibody, followed by standing at room temperature for 1 hour and then washing with washing buffer three times or more. The detection antibody was added to each well, followed by standing at room temperature for 1 hour and then washing with washing buffer three times or more. The secondary antibody was added, followed by standing at room temperature for 1 hour and then washing with washing buffer three times or more. TMB substrate was put in each well, followed by standing for 15 minutes under conditions of room temperature without light. Thereafter, 2 N sulfuric acid was added to step a chromic reaction, and then the absorbance was measured at 450 nm.

Figure 5:
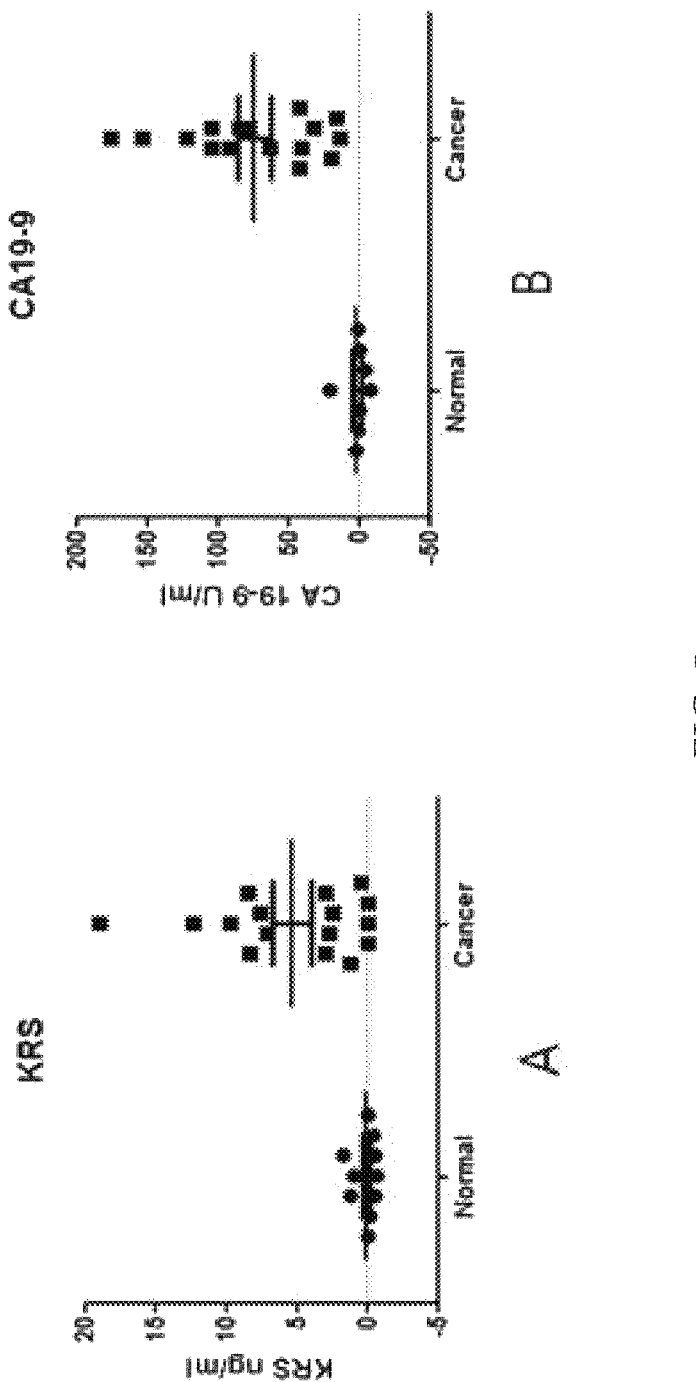
FIG. 5 illustrates results showing the level of KRS in the serum of normal persons and pancreatic cancer patients, measured by the ELISA method using the antibody of the present invention, in order to detect and mutually compare the blood KRS levels of normal persons and cancer patients using the antibody of the present invention (A: blood KRS concentration, B: blood CA19-9 concentration).

As shown in FIG. 5, it can be seen that KRS increased statistically significantly (p=0.003) in the pancreatic cancer patient group compared with the normal person group. When these results were compared with the measurement values (p=0.002) of CA19-9 as a representative single biomarker for pancreatic cancer, it can be seen that KRS is highly applicable as a diagnostic biomarker for pancreatic cancer, and it was validated that the anti-KRS antibody developed by the present applicant exhibited excellent effects as an antibody for the diagnosis of pancreatic cancer.

Furthermore, in order to investigate the importance and usefulness of KRS as a biomarker in the diagnosis of pancreatic cancer and compare and analyze with the measurement values of other candidate biomarkers, several candidate biomarkers were tested by using commercialized ELISA kit and multiplex bead assay kits. All the measured biomarkers were KRS, WRS, AIMP1, CA19-9, CA125, IL-8, CEA, TNF-α, and CEACAM-1, and the test results were expressed in a heatmap form.

The commercialized ELISA kit and multiplex bead assay kits were used according to the manufacturer's indications. For multiplex assay, antibody beads of each biomarker having a volume corresponding to 2000 beads were taken to adjust the final volume of 3 ml, and then 25 μl of the antibody beads were added to each well, and 25 μl of a specimen was added to each well. The mixture was stirred at 4☐, and then allowed to stand overnight. After each well was washed, 25 μl of the detection antibody was added, followed by standing at room temperature for 1.5 hours. 25 μl of streptavidin-phycoerythrin was added to each well, followed by standing at room temperature for 30 minutes and then washing. The measurement was performed on the plate using Luminex instrument (Bio-plex 200), and then the measurement results were analyzed using Median Fluorescent Intensity data.

Figure 6:
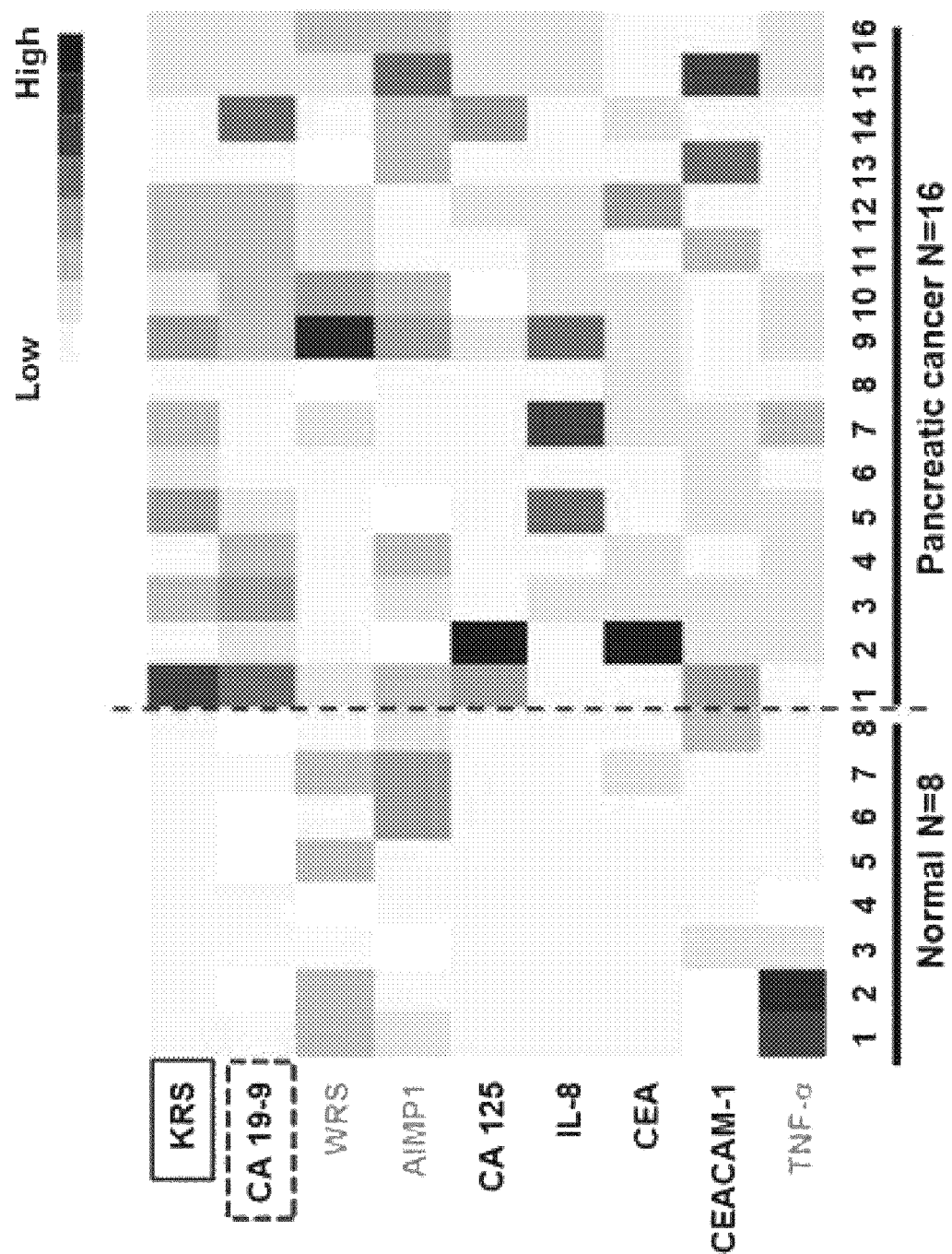
FIG. 6 illustrates comprehensive comparison and analysis results of biomarker quantitative values measured by ELISA and multiplex bead assay performed on several biomarker candidate groups, in order to investigate whether the measurement of the KRS biomarker using the antibody of the present invention is useful as a main biomarker for pancreatic cancer diagnosis.

As shown in FIG. 6, it can be seen that KRS and CA19-9, which is a representative single biomarker of pancreatic cancer, increased statistically significantly in the pancreatic cancer patient group compared with the normal person group. In addition, it can be seen that when compared with the measurement values of other candidate biomarkers, the usefulness of KRS is very highly applicable as a diagnostic biomarker of pancreatic cancer, and it could be validated that the anti-KRS antibody developed by the present applicant exhibited excellent effects as a diagnostic antibody for pancreatic cancer.

INDUSTRIAL APPLICABILITY

As set forth above, the antibody or fragment thereof of the present invention specifically binds to human KRS and has no cross activity with other proteins including the same ARS family, thereby enabling KRS detection and inhibition, so the antibody or fragment thereof of the present invention can be used for the purpose of detecting KRS and diagnosing cancer or autoimmune disease and inflammatory disease, which are diseases in association with KRS, and thus the present invention is highly industrially applicable.

The invention claimed is:

1. An antibody or fragment thereof that binds to human lysyl-tRNA Synthetase (KRS), the antibody comprising:
   an antibody light chain variable region (VL) comprising complementarity-determining region (CDR) L1 including the amino acid sequence represented by SEQ ID NO: 1, complementarity-determining region (CDR) L2 including the amino acid sequence represented by SEQ ID NO: 2, and complementarity-determining region (CDR) L3 including the amino acid sequence represented by SEQ ID NO: 3; and
   an antibody heavy chain variable region (VH) comprising complementarity-determining region (CDR) H1 including the amino acid sequence represented by SEQ ID NO: 4, complementarity-determining region (CDR) H2 including the amino acid sequence represented by SEQ ID NO: 5, and complementarity-determining region (CDR) H3 including the amino acid sequence represented by SEQ ID NO: 6.

2. The antibody or fragment thereof of claim 1, wherein the antibody comprises the 137th to 246th amino acid residues of the amino acid sequence of SEQ ID NO: 13 for the light chain variable region, and the 1st to 121st amino acid residues of the amino acid sequence of SEQ ID NO: 13 for the heavy chain variable region.

3. The antibody or fragment thereof of claim 1, wherein the antibody comprises the amino acid sequence represented by SEQ ID NO: 13.

4. The antibody or fragment thereof of claim 1, wherein the fragment is selected from the group consisting of diabody, Fab, Fab', F(ab)₂, F(ab')₂, Fv, and scFv fragments.

5. A polynucleotide encoding the antibody or fragment thereof of claim 1.

6. The polynucleotide of claim 5, wherein the polynucleotide comprises polynucleotides represented by SEQ ID NOs: 7 to 12.

7. A vector comprising the polynucleotide of claim 5.

8. A cell comprising the vector of claim 7.

9. A method for preparing an antibody or fragment thereof that binds to human KRS, the method comprising:
   culturing the cell of claim 8 under a condition where a polynucleotide is expressed, thereby preparing a polypeptide comprising light-chain and heavy-chain variable regions; and
   collecting the polypeptide from the cell or a culture medium in which the cell is cultured.

10. A method for detecting KRS in a subject, the method comprising:
   obtaining a biological sample from a subject;
   contacting the antibody or fragment thereof of claim 1 with the biological sample; and
   detecting binding between KRS in the biological sample and the antibody or fragment thereof.

11. A composition comprising the antibody or fragment thereof of claim 1 as an active ingredient for diagnosing a cancer, an autoimmune disease or an inflammatory disease.

12. A method for diagnosing a cancer, an autoimmune disease, or an inflammatory disease in a subject, the method comprising:
   (a) obtaining a biological sample from a subject;
   (b) determining the level of KRS protein in the biological sample using the antibody or fragment thereof of claim 1;
   (c) comparing the determined level of KRS protein with the level of KRS protein in a comparable sample from a normal subject; and
   (d) diagnosing the subject with a cancer, an autoimmune disease or an inflammatory disease when the determined level of KRS protein is higher than the level of KRS protein in the comparable sample from the normal subject.

* * * * *

UNITED STATES PATENT AND TRADEMARK OFFICE
CERTIFICATE OF CORRECTION

PATENT NO. : 9,945,859 B2  
APPLICATION NO. : 15/198337  
DATED : April 17, 2018  
INVENTOR(S) : Sunghoon Kim et al.

Page 1 of 1

It is certified that error appears in the above-identified patent and that said Letters Patent is hereby corrected as shown below:

On the Title Page

Column 1, Item (56), Other Publications, delete "p," and insert -- p. --, therefor.

In the Specification

Column 4, Line 46, delete "et." and insert -- et --, therefor.
Column 4, Line 60, delete "et." and insert -- et --, therefor.
Column 5, Line 16, after "variable domain" insert -- (VL) --.
Column 6, Line 39, delete "MRS" and insert -- KRS --, therefor.
Column 6, Line 42, delete "MRS" and insert -- KRS --, therefor.
Column 6, Line 43, delete "MRS" and insert -- KRS --, therefor.
Column 7, Line 14, delete "Rosenburg" and insert -- Rosenberg --, therefor.
Column 9, Line 41, delete "reesia" and insert -- reesei --, therefor.
Column 10, Line 26, delete "equivalent," and insert -- equivalent --, therefor.

Signed and Sealed this
Twenty-sixth Day of June, 2018

Andrei Iancu
*Director of the United States Patent and Trademark Office*